United States Patent
Martin et al.

(10) Patent No.: US 7,618,367 B2
(45) Date of Patent: Nov. 17, 2009

(54) THREE-PRONG RETRACTOR WITH ELASTOMERIC SHEATH

(75) Inventors: Greg Martin, Encinitas, CA (US); Mahmoud F. Abdelgany, Rockaway, NJ (US); William Bush, Westminster, MD (US)

(73) Assignee: Stryker Spine (FR)

(*) Notice: Subject to any disclaimer, the term of this patent is extended or adjusted under 35 U.S.C. 154(b) by 110 days.

(21) Appl. No.: 11/327,705

(22) Filed: Jan. 6, 2006
(Under 37 CFR 1.47)

(65) Prior Publication Data
US 2007/0021656 A1    Jan. 25, 2007

Related U.S. Application Data

(60) Provisional application No. 60/642,234, filed on Jan. 7, 2005.

(51) Int. Cl.
*A61B 1/32* (2006.01)

(52) U.S. Cl. .................. 600/224; 600/210; 600/214; 600/219

(58) Field of Classification Search ........... 600/214, 600/224, 231–233, 220, 222, 225, 228–229, 600/210, 219
See application file for complete search history.

(56) References Cited

U.S. PATENT DOCUMENTS

| | | | |
|---|---|---|---|
| 430,350 A | 6/1890 | McCully | |
| 1,275,520 A | 8/1918 | Bell | |
| 1,919,120 A | 7/1933 | O'Connor et al. | |
| 2,083,573 A | 6/1937 | Morgan | |
| 3,030,947 A | 4/1962 | Engelbert | |
| 3,044,461 A | 7/1962 | Murdock | |
| 4,263,899 A | 4/1981 | Burgin | |
| 4,597,383 A | 7/1986 | VanDerBel | |
| 4,726,356 A * | 2/1988 | Santilli et al. | 600/232 |
| 4,852,552 A * | 8/1989 | Chaux | 600/232 |
| 5,007,409 A | 4/1991 | Pope | |
| 5,178,133 A | 1/1993 | Pena | |
| 5,503,617 A | 4/1996 | Jako | |
| 5,667,520 A | 9/1997 | Bonutti | |
| 5,681,340 A | 10/1997 | Veronikis | |
| 5,755,661 A | 5/1998 | Schwartzman | |
| 5,792,044 A | 8/1998 | Foley et al. | |
| 5,795,291 A | 8/1998 | Koros et al. | |
| 5,813,978 A | 9/1998 | Jako | |
| 5,908,382 A * | 6/1999 | Koros et al. | 600/232 |
| 5,944,658 A | 8/1999 | Koros et al. | |

(Continued)

FOREIGN PATENT DOCUMENTS

DE    197 40 576 A1    4/1999

(Continued)

*Primary Examiner*—Cris L Rodriguez
*Assistant Examiner*—Hao D Mai
(74) *Attorney, Agent, or Firm*—Lerner, David, Littenberg, Krumholz & Mentlik, LLP

(57) ABSTRACT

A three-prong retractor is disclosed which is inserted into an incision in a patient in order to create an area for surgery. The retractor opens such that two blades move away from a first blade to create an elongated opening. The two blades may then move away from each other in a direction that intersects the direction of the movement of the first blade away from the two blades. The ends of the two blades remote from the retractor body may then move away from the end of the first blade remote from the retractor body to further open the incision. The retractor may also have an elastomeric sheath surrounding the blades in order to create a barrier between the surgical area and the patient's skin.

16 Claims, 4 Drawing Sheets

U.S. PATENT DOCUMENTS

| | | |
|---|---|---|
| 5,976,146 A | 11/1999 | Ogawa et al. |
| 6,036,638 A | 3/2000 | Nwawka |
| 6,083,154 A | 7/2000 | Liu et al. |
| 6,099,468 A * | 8/2000 | Santilli et al. ............... 600/232 |
| 6,099,547 A | 8/2000 | Gellman et al. |
| 6,139,493 A | 10/2000 | Koros et al. |
| 6,187,000 B1 | 2/2001 | Davison et al. |
| 6,224,545 B1 | 5/2001 | Cocchia et al. |
| 6,371,968 B1 | 4/2002 | Kogasaka et al. |
| 6,524,320 B2 | 2/2003 | DiPoto |
| 2002/0177753 A1 | 11/2002 | Dobrovolny |
| 2002/0183595 A1 | 12/2002 | Rioux et al. |
| 2003/0069477 A1 | 4/2003 | Raisman et al. |
| 2003/0149341 A1 | 8/2003 | Clifton |
| 2003/0191371 A1 | 10/2003 | Smith et al. |
| 2004/0002629 A1 | 1/2004 | Branch et al. |
| 2004/0133077 A1 | 7/2004 | Obenchain et al. |
| 2005/0070765 A1 * | 3/2005 | Abdelgany et al. .......... 600/214 |

FOREIGN PATENT DOCUMENTS

| | | |
|---|---|---|
| EP | 0 890 341 | 6/1908 |
| EP | 0 455 282 B1 | 11/1991 |
| EP | 0 614 646 A1 | 9/1994 |
| EP | 1 036 544 A1 | 9/2000 |
| WO | WO-94/21179 | 9/1994 |
| WO | WO-00/27291 A | 5/2000 |
| WO | WO-2004/062489 A1 | 7/2004 |

* cited by examiner

THREE-PRONG RETRACTOR WITH ELASTOMERIC SHEATH

CROSS REFERENCE TO RELATED APPLICATIONS

The present application claims benefit of U.S. Provisional Application No. 60/642,234, filed Jan. 7, 2005, the disclosure of which is hereby incorporated by reference herein.

BACKGROUND OF THE INVENTION

The present invention relates to a device used to retract the tissue of the body of a patient during surgery. More specifically, the present invention relates to a retractor that facilitates enlarging a surgical cavity and providing access to a surgical site.

Invasive surgical procedures require a surgeon to create an incision in the patient's skin in order to access the area within the patient's body where the surgery must be performed. It is desirable for the surgeon to create a small incision because a smaller incision takes less time to heal and thus causes less trauma to the patient. The incision, however, must be large enough to accommodate the surgeon's tools necessary to perform the surgery. Thus, retractors are often used to hold open incisions in order to hold a patient's skin wide open for surgery and prevent the skin from entering the surgery area while the surgeon operates his or her tools.

Retractors as known in the art typically consist of two opposing prongs that enter into an incision and extend away from each other in order to pull the skin of the patient back into a large opening. These retractors pose two problems: the opening created by the retractor is an elongated opening that is usually not large enough to accommodate a plurality of surgical tools, and there is no protection of the skin from the surgical area which may lead to the slippage of surgical tools on to the skin of the patient. Thus, a need exists for a surgical retractor that provides a large surgical work area from a small incision and creates a boundary between the surgical area and the patient's skin.

The present invention addresses these needs by facilitating a larger surgical cavity for surgery through a smaller incision which minimizes tissue trauma. This minimally-invasive approach provides faster patient rehabilitation than traditional incision and retraction techniques.

The various embodiments of the present invention are particularly useful for orthopedic surgery of the spine, but are envisioned to be limitlessly applicable to other surgical techniques and other parts of the body.

SUMMARY OF THE INVENTION

In a preferred embodiment the present invention is a retractor comprising a first supporting member, a second supporting member coupled to said first supporting member for selective translational movement of said first and second supporting members towards and away from each other, a holding arm connected to said second supporting member on an axis, a medial blade attached to said first supporting member having a distal end remote from the first supporting member, and a pair of lateral blades attached to said holding arm, each of said lateral blades having a distal end remote from said holding arm, said holding arm facilitating movement of said ends toward and away from each other in a plane that intersects the direction of the translational movement of said first supporting member and said second supporting member. The holding arm preferably rotates such that the distal ends of the lateral blades rotate away from the medial blade. An actuator may facilitate this rotation.

In one aspect, the medial blade and the lateral blades are preferably surrounded by a sheath. The sheath may be an elastomeric sheath made of silicone rubber. The sheath may be partially transparent or translucent.

In a further aspect, the medial blade and the lateral blades are pivotally connected to the first supporting member and the holding arm. The blades may be made of a polymer or of aluminum. The blades may be of different lengths for a particular surgery. For example, the lateral blades may be shorter than the medial blade or the medial blade may be shorter than the lateral blades. In one embodiment, the distal ends of the blades may be tapered. One or more of the blades may be curved in a horizontal plane.

In another embodiment, the present invention is a retractor comprising a first supporting member, a second supporting member coupled to the first supporting member, a holding arm connected to said second supporting member on an axis, a medial blade attached to said first supporting member at a proximal end and having a distal end remote to the first supporting member, a pair of lateral blades attached to said holding arm, each of said lateral blades having an end remote from said holding arm, means for moving the second supporting member away from the first supporting member, and means for moving the ends of the lateral blades away from each other. The retractor may also comprise means for rotating the ends of the lateral blades away from the end of the medial blade.

In this embodiment, the medial blade and the pair of lateral blades are preferably surrounded by a sheath, which may be an elastomeric sheath.

In another aspect of this embodiment, the medial blade is shorter than the pair of lateral blades.

In yet another aspect, the present invention comprises a method of retracting tissue from an incision for surgery comprising the steps of inserting three blades of a retractor having one medial blade having an end and two lateral blades having ends into an incision, actuating the retractor to move the medial blade away from the two lateral blades, actuating the retractor to move the ends of the two lateral blades away from each other, and actuating the retractor to move the ends of the two lateral blades away from the end of the medial blade.

DETAILED DESCRIPTION

Figure 1A:
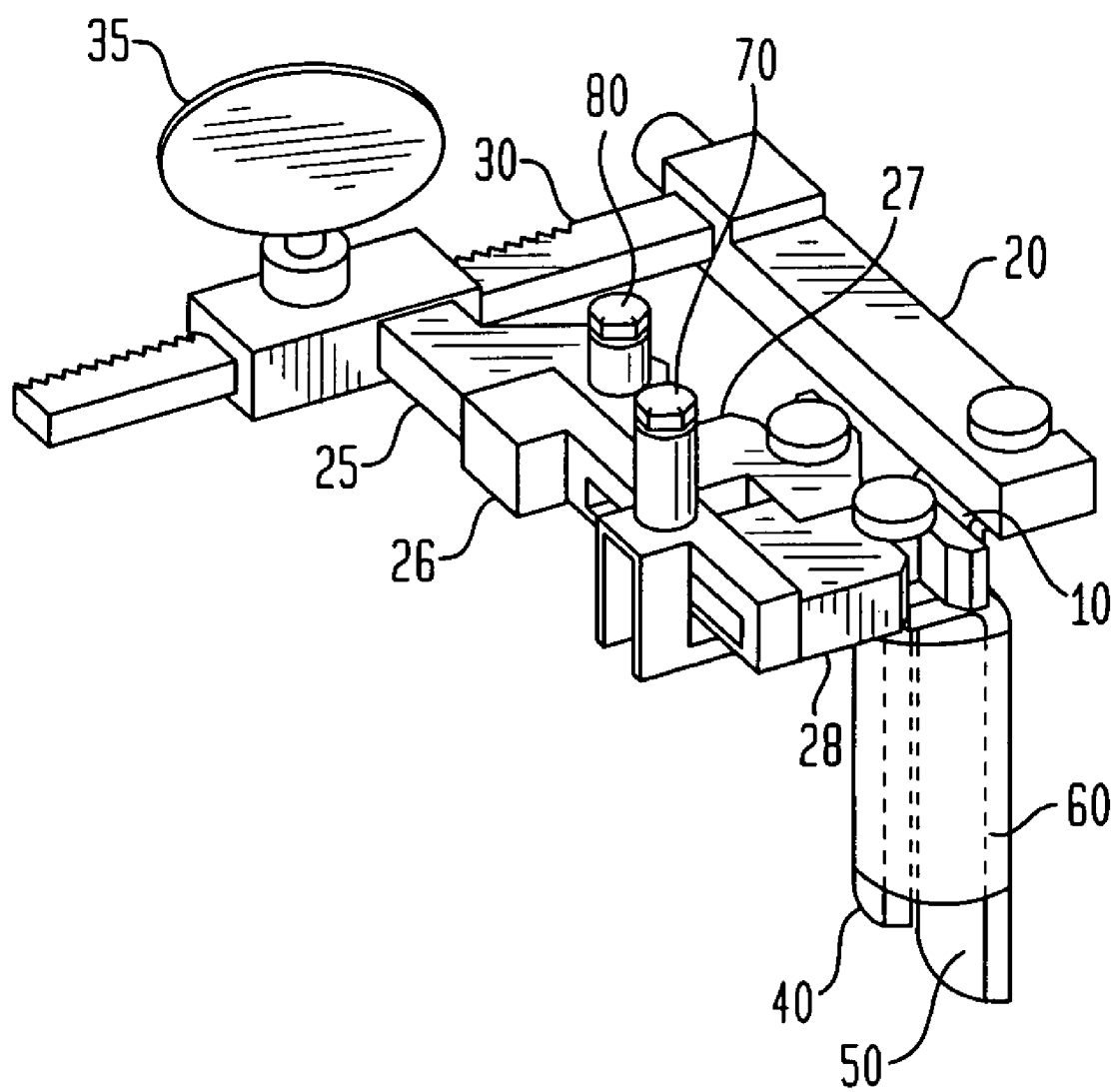
FIG. 1A is a top perspective view of one embodiment of a retractor according to the present invention.
Figure 1B:
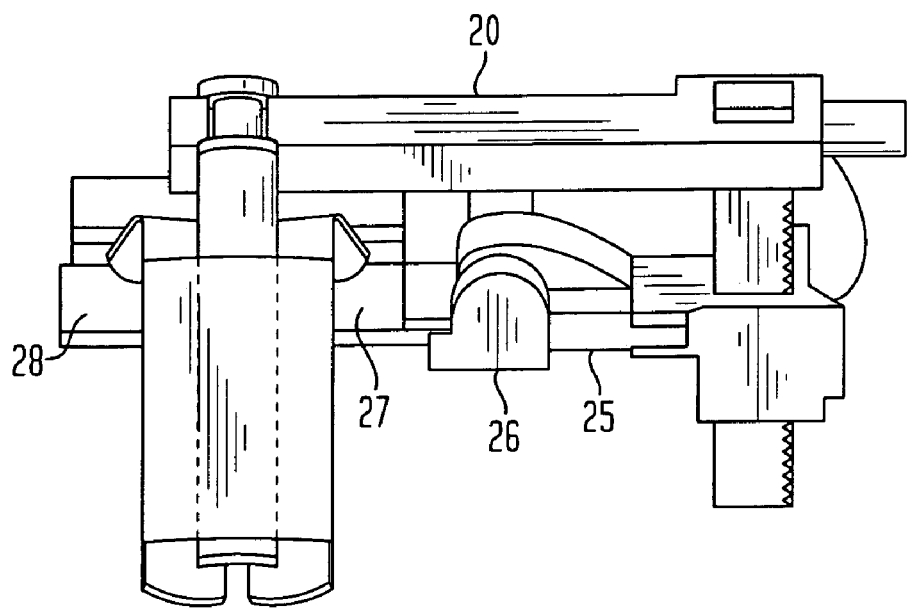
FIG. 1B is a bottom perspective view of the retractor depicted in FIG. 1A.

FIGS. 1A and 1B depict one embodiment of the versatile frame retractor according to the present invention in a closed position for insertion into an incision. The medial blade 10 is attached to a first supporting member 20, which is coupled to the second supporting member 25 with a rack member 30 and crank 35, or other expedient as known in the art. The second supporting member 25 is connected to the holding arm 26, which holds the first retaining member 27 and the second retaining member 28. The first lateral blade 40 and second lateral blade 50 are held by the first retaining member 27 and the second retaining member 28. The first lateral blade 40 and second lateral blade 50 are positioned against the medial blade 10 for ease of insertion of the retractor into a small incision. The medial blade 10 is preferably shorter than the lateral blades to better accommodate the anatomy of the spine; specifically the arch of the lamina and the greater depth of the transverse process. The three blades are preferably surrounded by an elastomeric sheath 60 which prevents tissue from entering the surgical site while the surgeon is working. The frame retractor further comprises a central drive screw 70 and a second drive screw 80.

Figure 3:
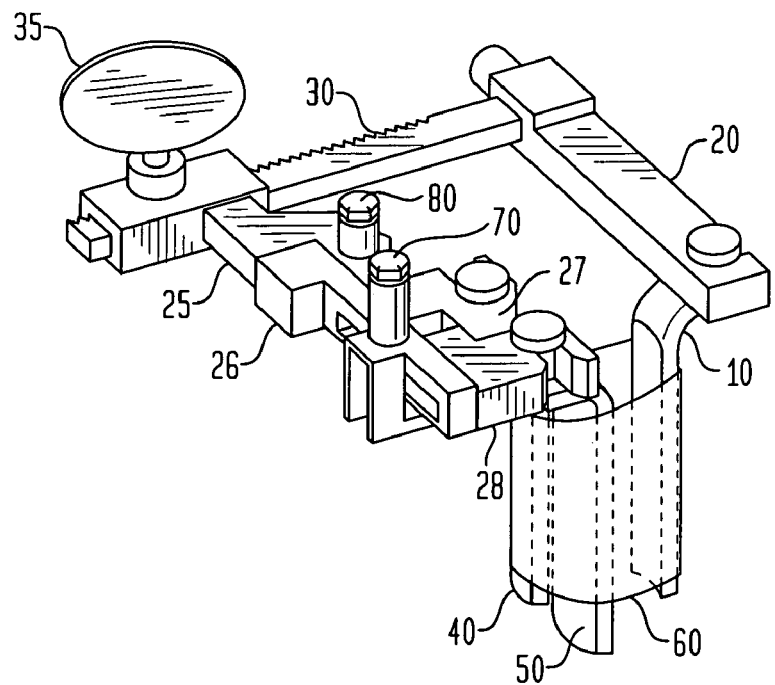
FIG. 3 is a top perspective view of the retractor in a translated position.

The medial blade and the lateral blades are preferably curved in the horizontal plane as best seen in FIG. 3 so that the blades exert less stress on the tissue while the retractor is in the opened position. In addition, each of the blades may have a small lip or tapered end where they are to be inserted into tissue to prevent the blades from slipping out of the tissue while the retractor is in use.

Figure 2:
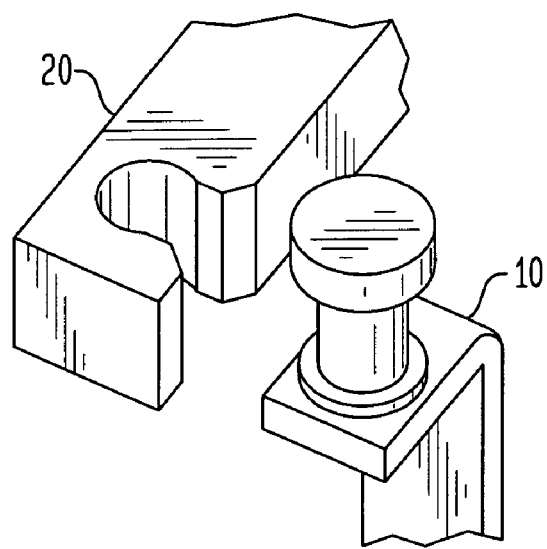
FIG. 2 is an enlarged perspective view of the connection between the medial blade of the retractor and the first supporting member.

FIG. 2 is an enlargement depicting the connection of the medial blade 10 to the first supporting member 20, which includes a key slot with a rectangular channel communicating with a round opening. The medial blade 10 includes a post with a round head, the post including flats which permit the post to be entered into the rectangular slot. The medial blade 10 can then be rotated and captured in the round opening. The first lateral blade 40 and the second lateral blade 50 are connected to the first retaining member 27 and the second retaining member 28 in the same or a similar fashion, though it is recognized that any suitable expedient can be practiced. Alternatively, one or more of the blades may be integrally or permanently attached to the respective portions of the frame retractor.

The terms "sagittal" and "transverse" as used herein refer to the orientation of the retractor with respect to the surgeon. These terms are used herein for convenience only. One skilled in the art would recognize a plurality of options for positioning the retractor in a patient depending on the type of surgery and preference of the surgeon. In this application, "sagittal plane" means that the ends of the blades are rotated away from each other in a plane that intersects the direction of the translational movement of the first supporting member 20 and the second supporting member 25. The term "transverse plane" means that the ends of the lateral blades 40, 50 are rotated away from the end of the medial blade 10 in the same direction that the first supporting member 20 and the second supporting member 25 are translated away from each other.

The blades 10, 40, and 50 of the retractor are preferably easily removable. This allows a surgeon to replace the blades with longer or shorter blades as the surgery and/or anatomy requires. In addition, easy removal of the blades provides for sterilization or disposability. Thus, a surgeon may be provided with a kit of variably sized and shaped blades from which desired blades may be selected for a particular surgery or technique. Additionally, disposability of the blades allows for easier post-use handling techniques.

To use the retractor, the surgeon makes a small incision in the skin of the patient and inserts the distal ends of the blades, meaning the ends of the blades that are not attracted to the body of the retractor, into the incision. The retractor is preferably in a closed position as shown in FIG. 1A when inserted into the incision. Once the blades of the retractor are inserted into the incision, the crank 35 may be rotated to translate the second supporting member 25 away from the first supporting member 20 as depicted in FIG. 3. This will force the lateral blades 40, 50 away from the medial blade 10 and open the incision in preparation for surgery. As seen in FIG. 3, the elastomeric sheath 60 is flexible and will stretch to keep unwanted tissue out of the surgery area and protect the skin outside the surgery area from the surgical tools.

Figure 4:
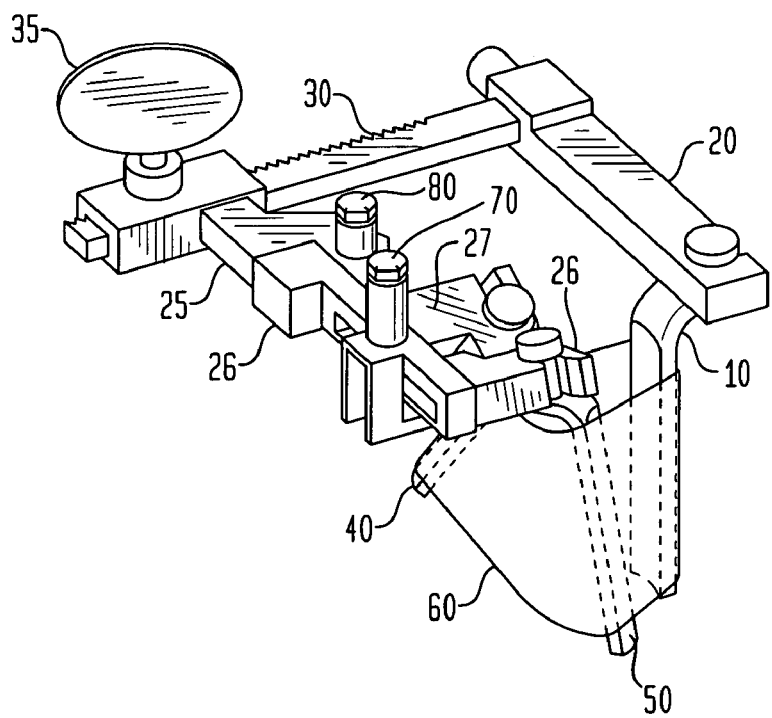
FIG. 4 is a top perspective view of the retractor with the lateral blades rotated in the sagittal plane.

To gain greater access to the surgical site, the lateral blades 40, 50 may be rotated in the sagittal plane by rotating the central drive screw 70 as shown in FIG. 4. The central drive screw is connected to an actuator that will rotate the first retaining member 27 and the second retaining member 28 away from each other. The blades will rotate within their retaining members to provide more access to the opening.

Figure 5:
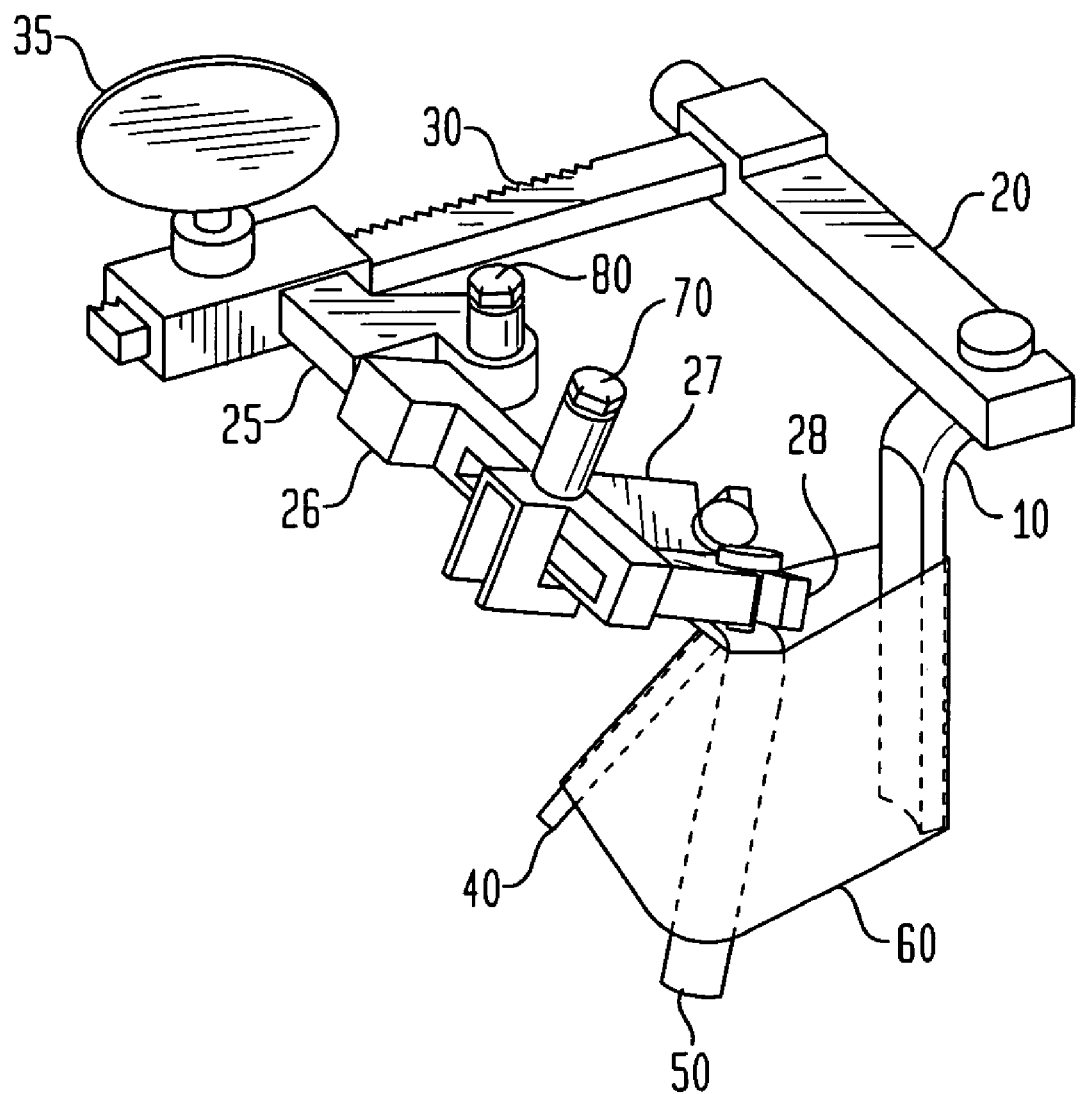
FIG. 5 is a top perspective view of the retractor with the lateral blades rotated in the sagittal plane and transverse plane.

If a larger opening is still desired, the second drive screw 80 may be rotated to angulate the holding arm in the transverse plane as shown in FIG. 5. The second drive screw 80 facilitates this rotation. The larger opening created by this rotation will provide the surgeon with a relatively large, clear view of the surgical site.

It is recognized that the central drive screw 70 and the second drive screw 80 may be engaged by a tool, such as a screwdriver, an Allen wrench, or any other suitable tool that will facilitate rotation. Additionally, it is envisioned that multiple variations of the type of tool, the interface with the screw, as well as screw types, or even the absence of a screw, are possible to facilitate the movement of the blades of the retractor towards and away from each other.

The material used in the construction of blades 10, 40, and 50 is generally of a rigid type, such as plastic or metal, to support the spreading of body tissue. In a preferred embodiment, the material is radiolucent or semi-radiolucent thereby allowing for the improved visualization of the anatomy when viewed on an X-ray with the retractor in place or to carry and emit light. In other embodiments, the material may be non-autoclavable or otherwise non-sterilizable, and disposable. This further allows for the interchangeability of blades to suit particular surgical applications as well as surgical cavity sizes.

The elastomeric sheath 60 is preferably made of a pliable, elastic, and preferably translucent material, such as silicone rubber, and fits snugly around the blades 10, 40, and 50. Preferably, the sheath 60 is assembled over the blades when the retractor is in the unexpanded position, as depicted in FIG. 1. Upon opening of the retractor as depicted in FIGS. 3, 4 and 5 the sheath 60 stretches and forms an enclosure around the blades 10, 40 and 50. This enclosure allows for a more manageable surgical cavity by preventing tissue from entering the cavity. The sheath 60 may also be made of a transparent material, so that when in the expanded condition, a surgeon may see tissue and objects through the sheath when it is in the surgical cavity.

Upon the reverse translation of the central drive screw 70 and second drive screw 80 and the return of the blades 10, 40 and 50 to their unexpanded state, the sheath 60 returns to its original form as well. Thus, when surgery has been completed, the blades of the retractor are brought together following the opposite steps used to expand the retractor. Once the blades are completely together as shown in FIG. 1A, the retractor may be removed from the incision. Depending on the pliability of the material used to construct the sheath, the sheath may aid in bringing the blades back to their original, unexpanded condition. In any event, the tissue surrounding the blades aids in compressing the blades back to their unexpanded condition. It should be noted that various materials with the above desirable properties for the sheath may improve the cost-effectiveness of the sheath's disposability. In addition, the sheath may be of any shape or size and may cover any area of the retractor, thereby creating any portion of covered and non-covered areas of the blades. The sheath may be interchangeable with other types of retractors, such as the surgical retractor with scissor arms disclosed in U.S. patent application Ser. No. 10/943,520, the entire disclosure of which is hereby incorporated by reference as fully set forth herein.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A retractor comprising:
  a first supporting member, the first supporting member having a first rectangular slot communicating with a first round opening;
  a second supporting member coupled to said first supporting member for selective translational movement of said first and second supporting members in a direction towards and away from each other;
  a holding arm connected to said second supporting member on an axis;
  a first retaining member attached to the holding arm, the first retaining member having a second rectangular slot communicating with a second round opening;
  a second retaining member attached to the holding arm, the second retaining member having a third rectangular slot communicating with a third round opening;
  a medial blade attached to said first supporting member, the medial blade having a distal end remote from the first supporting member, the medial blade having a first post, at least one first flat formed on the first post to allow the first post to slide in the first rectangular slot for quick and easy assembly and disassembly of the medial blade to the first supporting member; and
  a first lateral blade attached to the first retaining member and a second lateral blade attached to the second retaining member, each of said lateral blades having a distal end remote from said holding arm, and the lateral blades having a first drive screw and a second drive screw attached thereto, wherein operating the first drive screw simultaneously moves the distal ends toward and away from each other in a plane that intersects the direction of the translational movement of said first supporting member and said second supporting member, and operating the second drive screw simultaneously rotates the distal ends of the lateral blades away from the medial blade, and wherein the first lateral blade has a second post, at least one second flat formed on the second post to allow the second post to slide in the second rectangular slot for quick and easy assembly and disassembly of the first lateral blade to the first retaining member, and wherein the second lateral blade has a third post, and at least one third flat formed on the third post to allow the third post to slide in the third rectangular slot for quick and easy assembly and disassembly of the second lateral blade to the second retaining member.

2. The retractor of claim 1 wherein an actuator rotates the holding arm in a transverse plane.

3. The retractor of claim 1 wherein said medial blade and said lateral blades are surrounded by a sheath.

4. The retractor of claim 3 wherein said sheath is an elastomeric sheath.

5. The retractor of claim 1 wherein said medial blade is pivotally connected to the first supporting member and said lateral blades are pivotally connected to said holding arm.

6. The retractor of claim 3 wherein said elastomeric sheath is at least partially transparent or translucent.

7. The retractor of claim 1 wherein said lateral blades and said medial blade are made of a polymer.

8. The retractor of claim 1 wherein said medial blade and said lateral blades are composed of aluminum.

9. The retractor of claim 1 wherein at least one of said blades is shorter than at least one other blade to accommodate the anatomy of a surgical site in which the retractor is adapted to be used.

10. The retractor of claim 9 wherein the medial blade is shorter than the pair of lateral blades.

11. The retractor of claim 9 wherein the lateral blades are shorter than the medial blade.

12. The retractor of claim 1 wherein at least one of the lateral blades or the medial blade has a tapered distal end.

13. The retractor of claim 1 wherein at least one of the two lateral blades or the medial blade is curved in a horizontal plane.

14. A retractor comprising:
  (a) a first supporting member, the first supporting member having a first rectangular slot communicating with a first round opening;
  (b) a second supporting member coupled to said first supporting member;
  (c) a holding arm connected to said second supporting member on an axis;
  (d) a first retaining member attached to the holding arm, the first retaining member having a second rectangular slot communicating with a second round opening;
  (e) a second retaining member attached to the holding arm, the second retaining member having a third rectangular slot communicating with a third round opening;
  (f) a medial blade attached to said first supporting member at a proximal end and having a distal end remote to the first supporting member, the medial blade having a first post, at least one first flat formed on the first post to allow the first post to slide in the first rectangular slot for quick and easy assembly and disassembly of the medial blade to the first supporting member;
  (g) a first and a second lateral blade attached to a first and a second retaining member respectively, each of said lateral blades having an end remote from said holding arm, and wherein the first lateral blade has a second post, at least one second flat formed on the second post to allow the second post to slide in the second rectangular slot for quick and easy assembly and disassembly of the first lateral blade to the first retaining member, and wherein the second lateral blade has a third post, and at least one third flat formed on the third post to allow the third post to slide in the third rectangular slot for quick and easy assembly and disassembly of the second lateral blade to the second retaining member;

(h) means for moving the second supporting member away from the first supporting member;
(i) means for simultaneously moving the ends of the lateral blades away from each other; and
(j) means for simultaneously rotating the ends of the lateral blades away from the distal end of the medial blade.

15. The retractor of claim 14 wherein the medial blade and the pair of lateral blades are surrounded by a sheath.

16. The retractor of claim 14 wherein the medial blade is shorter than the pair of lateral blades.

* * * * *